US011915825B2

United States Patent
Galloway et al.

(10) Patent No.: US 11,915,825 B2
(45) Date of Patent: Feb. 27, 2024

(54) SYSTEMS AND METHODS OF ANALYTE MEASUREMENT ANALYSIS

(71) Applicant: AliveCor, Inc., Mountain View, CA (US)

(72) Inventors: Conner Daniel Cross Galloway, Sunnyvale, CA (US); Alexander Vainius Valys, Sunnyvale, CA (US); Frank Losasso Petterson, Los Altos Hills, CA (US); Daniel Treiman, San Francisco, CA (US)

(73) Assignee: AliveCor, Inc., Mountain View, CA (US)

( * ) Notice: Subject to any disclaimer, the term of this patent is extended or adjusted under 35 U.S.C. 154(b) by 1521 days.

(21) Appl. No.: 15/894,775

(22) Filed: Feb. 12, 2018

(65) Prior Publication Data

US 2018/0233227 A1    Aug. 16, 2018

Related U.S. Application Data

(60) Provisional application No. 62/570,432, filed on Oct. 10, 2017, provisional application No. 62/457,713, filed on Feb. 10, 2017.

(51) Int. Cl.
  *G06N 20/00*   (2019.01)
  *G06N 3/08*    (2023.01)
  (Continued)

(52) U.S. Cl.
  CPC ......... *G16H 50/20* (2018.01); *A61B 5/14546* (2013.01); *A61B 5/349* (2021.01);
  (Continued)

(58) Field of Classification Search
  CPC ....... G06N 20/00; G06N 3/08; A61B 5/14546
  See application file for complete search history.

(56) References Cited

U.S. PATENT DOCUMENTS 6,263,238 B1   7/2001   Brewer et al.
8,948,854 B2   2/2015   Friedman et al.
(Continued)

FOREIGN PATENT DOCUMENTS

IL       224207        5/2016
WO    2015/048514 A1   4/2015
(Continued)

OTHER PUBLICATIONS

Rahhal et. al., "Deep learning approach for active classification of electrocardiogram signals", Feb. 2016 (Year: 2016).*
(Continued)

*Primary Examiner* — Selene A. Haedi
(74) *Attorney, Agent, or Firm* — Womble Bond Dickinson (US) LLP

(57) ABSTRACT

Disclosed systems include an electrocardiogram sensor and a processing device operatively coupled to the electrocardiogram sensor. The processing device receives electrocardiogram data from the electrocardiogram sensor and applies a machine learning model to the received electrocardiogram data. The machine learning model has been trained based on previous electrocardiogram data of a plurality of subjects. The electrocardiogram data of the plurality of subjects have one or more associated analyte measurements. The processing device may determine an indication of a level of the analyte based on the electrocardiogram data.

15 Claims, 9 Drawing Sheets

(51) Int. Cl.
    *A61B 5/145* (2006.01)
    *G16H 50/20* (2018.01)
    *G06N 3/04* (2023.01)
    *A61B 5/00* (2006.01)
    *A61B 5/349* (2021.01)
    *G06N 3/044* (2023.01)
    *G06N 3/045* (2023.01)
    *A61B 5/25* (2021.01)

(52) U.S. Cl.
CPC ............. *A61B 5/7267* (2013.01); *G06N 3/04* (2013.01); *G06N 3/044* (2023.01); *G06N 3/045* (2023.01); *G06N 3/08* (2013.01); *G06N 20/00* (2019.01); *A61B 5/25* (2021.01); *A61B 5/743* (2013.01)

(56) References Cited

U.S. PATENT DOCUMENTS

| | | | |
|---|---|---|---|
| 9,307,921 | B2 | 4/2016 | Friedman et al. |
| 9,414,786 | B1 | 8/2016 | Brockway et al. |
| 9,907,478 | B2 | 3/2018 | Friedman et al. |
| 2008/0167567 | A1* | 7/2008 | Bashour .................. A61B 5/352 600/521 |
| 2013/0346351 | A1* | 12/2013 | Lin ........................ G06N 20/00 706/21 |
| 2016/0256063 | A1 | 9/2016 | Friedman et al. |
| 2017/0098172 | A1* | 4/2017 | Ellenbogen ............. H04L 43/04 |
| 2017/0112401 | A1* | 4/2017 | Rapin ................... A61B 5/7203 |
| 2017/0340292 | A1* | 11/2017 | Rossi ..................... A61B 5/364 |
| 2018/0350468 | A1* | 12/2018 | Friedman ........... A61B 5/14546 |

FOREIGN PATENT DOCUMENTS

| | | |
|---|---|---|
| WO | 2016/038585 A1 | 3/2016 |
| WO | 2017/091736 A1 | 6/2017 |
| WO | 2018/049402 A1 | 3/2018 |

OTHER PUBLICATIONS

Dillon et al., "Noninvasive potassium determination using a mathematically processed ECG: Proof of concept for a novel blood-less, blood test", 2015 (Year: 2015).*
International Search Report and Written Opinion for International Application No. PCT/US2017/066500.
Invitation to Pay Additional Fees for International Application No. PCT/US2018/017880.
Porter et al., "Prediction of Hyperkalemia in Dogs from Electrocardiogramaparameters Using an Artificial Neural Network", Academic Emergency Medicine, vol. 8, No. 6, Jun. 2001, pp. 599-603.
Supratak et al., "Survey on Feature Extraction and Applications on Biosignals" ECCV 2016 Conference, Springer International Publishing, Dec. 10, 2016, pp. 161-182.
Tzeng et al., "Predicting Hyperkalemia by the Use of a 12-Lead Temporal-Spatial Electrocardiogramical Evaluations and Model Simulations", Computers in Cardiology, Lyon, France, IEEE, Piscataway, NJ, USA, Sep. 25, 2005, pp. 215-218.
Wu et al., "Predicting Hyperkalemia by a Two-Staged Artificial Neural Network", Computers in Cardiology, New York, NY, US, IEEE, vol. 30, Sep. 21, 2003, pp. 433-436.
Response to Office Action filed Feb. 28, 2018 in U.S. Appl. No. 15/025,158.
U.S. Appl. No. 62/258,956, filed Nov. 23, 2015.
U.S. Appl. No. 62/401,044, filed Sep. 28, 2016.

* cited by examiner

SYSTEMS AND METHODS OF ANALYTE MEASUREMENT ANALYSIS

CROSS-REFERENCE TO RELATED APPLICATIONS

This application claims the benefit of U.S. Provisional Application No. 62/457,713 filed on Feb. 10, 2017, the entire contents of which are hereby incorporated by reference.

BACKGROUND

Electrolytes are tightly regulated within the healthy mammalian body. For example, potassium, magnesium and calcium are essential electrolytes used by the body in numerous physiological processes, where a relatively small deviation in electrolyte concentration outside of a normal range may lead to serious complications within an individual. For example deviation of potassium concentration, hypokalemia and hyperkalemia, is associated with cardiac arrest.

Electrolytes and other substances within the mammalian body may be monitored invasively through, for example, drawing a blood sample from an individual and analyzing the blood sample to determine a concentration of the electrolyte or other substance within the sample.

DETAILED DESCRIPTION

Figure 1:
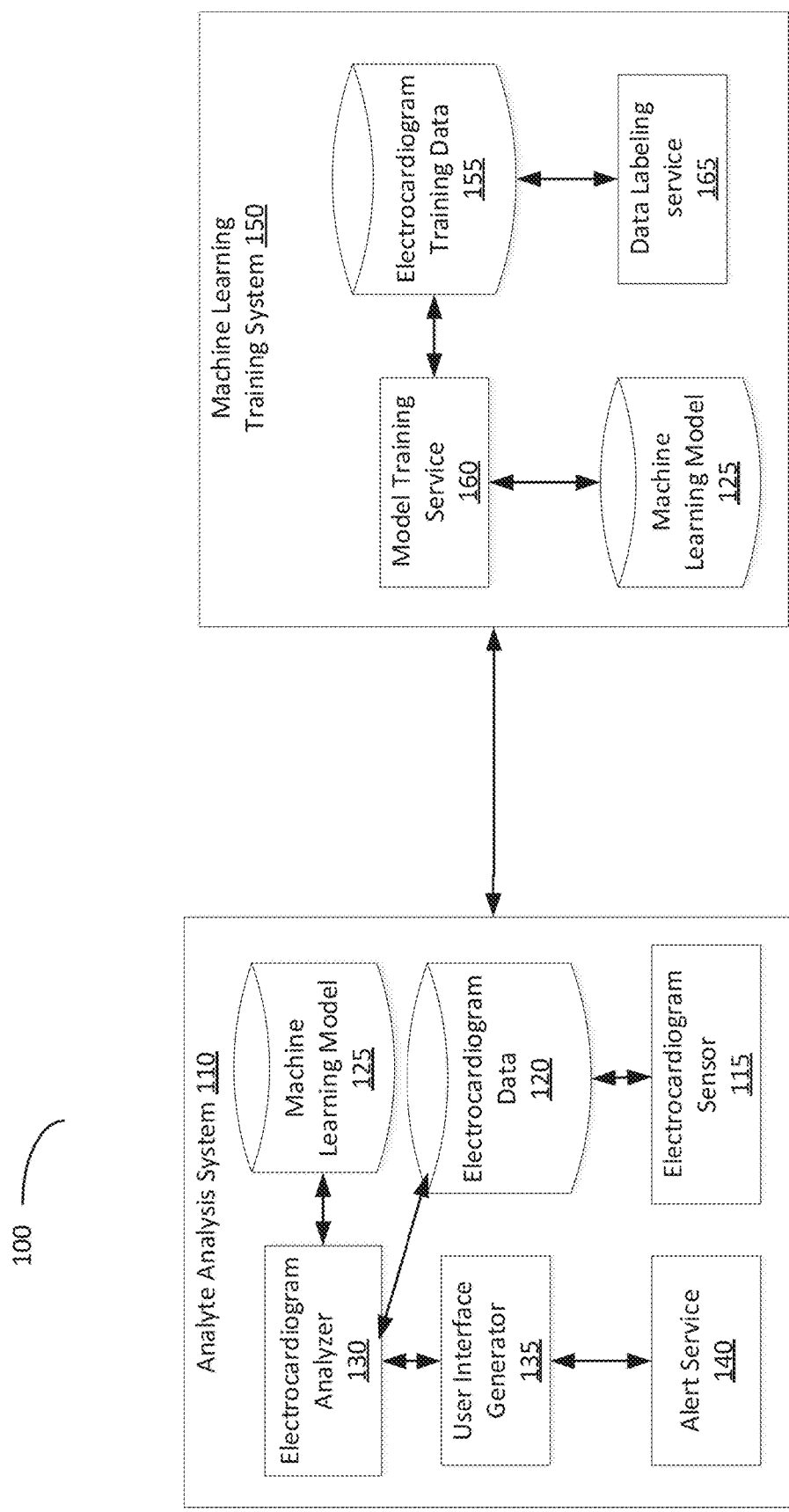
FIG. 1 illustrates an example system to provide analyte measurement as discussed herein, according to aspects of the disclosure.

Described herein are non-invasive devices and techniques for monitoring a level of a substance within the body of a subject, and more particularly concentrations of analytes including serum or plasma concentrations. The non-invasive technique described herein includes sensing a biosignal such as an electrocardiogram of an individual and analyzing the biosignal to determine a concentration of a substance within the body of the subject based on analysis of the biosignal. Analyzing the biosignal may include inputting the biosignal to a machine learning model that was trained on training examples of previous biosignals recorded from a population of individuals.

Training a machine learning model may include receiving electrocardiograms of a number of subjects and associated analyte measurements of those subjects ("labels"). The machine learning model can then be trained on the example training data and associated measurements. In some embodiments, the associated analyte measurements may be subject to some error or uncertainty, for example the error of the process used to determine an analyte measurement from a blood sample. In order to train the machine learning model, the training data may be processed to filter or adjust the labeling of the training data prior to training the system.

In particular, errors in the training data may cause reduced accuracy of a trained machine learning model, or may make it difficult to accurately assess the performance of a given model during or after the training process. This problem may be particularly pronounced when the distribution of analyte measurements is non-uniform, as is the case for many. For example, errors may be more significant to the training of a machine learning model if there are few samples with a particular label. Notably, if the prevalence of a certain label in the training data and the error rate in the associated measurement for that label are of a similar order of magnitude, a significant number of samples with that label may be inaccurately labeled. Those inaccurately labeled samples can reduce the effectiveness of training the machine learning model and the overall accuracy of the model as applied to samples of subjects.

In some embodiments, identifying and filtering potentially inaccurate measurements or labeling data can be done by setting rules for when data may be considered accurate or when it is excluded because the correct label cannot be determined. For example, in some embodiments, a training dataset may consist of a series of timestamped electrocardiogram (ECG) recordings from a multitude of individuals, and timestamped analyte measurements performed by blood draw around the same time as the ECG. If two (or more) blood draws within a certain period of time result in consistent results, e.g., analyte considered "high", "normal", or "low" in both results, then the result may be considered reliable for labeling. If the two blood draws, in this example, produce inconsistent results, that ECG and associated labeling data is removed from the training data set. Some additional rules may determine a maximum or minimum amount of time between an electrocardiogram and a blood analyte level to select which data to filter from the training examples. In some embodiments, additional rules may only label an electrocardiogram for a sample as high, low or normal if there are multiple measurements of an analyte value that are consistent with that finding. The skilled artisan will appreciate that other filtering rules may be used to select which ECG and associated labels to include in the training data.

In some embodiments, rather than filtering data based on heuristic rules, an estimated range of an analyte level at a time of an ECG may be determined. For example, if there are multiple analyte measurements within 12 hours of any given ECG, a regression between the measurements may be used to determine an estimate of the analyte level. In some embodiments a Gaussian Process Regression (GPR) analysis may be used to determine an estimated level and a confidence interval around the estimated level at the time of ECG acquisition: for instance, the analyte concentration at a specific time may be estimated to be 5.2 mmol/L, with an uncertainty at 1 standard deviation of +/−0.4 mmol/L. The output of the GPR analysis at the time of the electrocardiogram may then be used to determine a level of the blood analyte level used to label the training sample. In some embodiments, the electrocardiogram may then be labeled or filtered based on the estimated analyte level and confidence interval. For example, the electrocardiogram may be labeled as corresponding to a 'high' analyte level if the estimated analyte level is above a threshold to be considered high and the confidence interval provides a certainty that the error on the estimated level is also above a given threshold: for instance, one could label an electrocardiogram as "high" only if both ends of the uncertainty interval at 1 standard deviation are above the threshold to be considered high. For example, if 5.0 mmol/L is the threshold for being considered "high", an electrocardiogram with an estimated analyte concentration of 5.2 mmol/L with an uncertainty of +/−0.4 mmol/L would not be considered high, because the lower bound of the uncertainty interval (4.8 mmol/L) is below the threshold. However, an electrocardiogram with an estimated analyte concentration of 5.8 mmol/L and an uncertainty of +/−0.6 mmol/L would be considered high.

In some embodiments, electrocardiogram data that has a confidence interval greater than a threshold confidence interval may be removed from the training set: for instance, any electrocardiogram with an uncertainty greater than 0.5 mmol/L could be excluded. Electrocardiogram data may also be removed if the confidence interval falls both above and below a threshold for a high analyte level: in the example above, rather than simply not labeling an electrocardiogram as "high", the electrocardiogram can be removed from the training set entirely if the correct label cannot be determined within a specified tolerance. In some embodiments, electrocardiogram data may also be labeled with an indication of the confidence interval or an estimated error amount. Rather than excluding files, the machine learning model may be trained by providing a lower penalty on errors made on the output of labeled data that has lower certainty than the penalty on the output of labeled data that has a higher certainty.

While the description herein is generally discussed with respect to filtering and processing data with respect to training a machine learning model related to predicting analyte measurements based on a biosignal, such as an electrocardiogram, in various embodiments filtering, labelling, and training a machine learning model as described can be applied to other machine learning systems. For example, other biosignals such as heart rate variability, heart rate, temperature, or other biosignals can be used. In addition, other conditions than analyte concentration may be determined by a machine learning model based on one or more biosignals of a subject. Additionally, the filtering and exclusion of certain data may be provided in additional contexts outside of the medical fields. For example, any other application with a small portion of a certain label and a corresponding error rate creating significant potential error during training based on the error rate may process and filter training data as described herein. Accordingly, other training data with different input signals and output measurements may also be filtered and processed based on GPR analysis or other rules to improve a set of training data for training a machine learning model.

The numeric concentrations and thresholds described in the discussion above (e.g. 5.0 mmol/L) are merely examples. Specific concentrations and thresholds used in any particular embodiment should be chosen based on factors including by way of example the analyte being measured, the error rate in the technique used to produce those measurements, and the level of accuracy required in the resulting model.

In some embodiments, non-invasively determined analyte levels can include electrolytes such as, for example, potassium, magnesium, or calcium, other substances within a body may also be determined from analysis of an electrocardiogram. For example, a level of glucose within the body of an individual, a level of a pharmaceutical or pharmaceutical byproduct within the body of an individual, a level of alcohol or other drugs, or other substances may be determined from analysis of an electrocardiogram or other biological signals.

An electrocardiogram may be described with a number of features. Some of the common features viewed during analysis of an electrocardiogram include a P wave, QRS waves commonly referred to as a QRS complex, and a T wave. Other features may also be viewed in different electrocardiograms of different individuals. The level of certain analytes within the blood of an individual (e.g. potassium) may have an effect on that individual's electrocardiogram. For example, certain analytes may change a slope, amplitude, duration, smoothness, or other characteristics of a feature of an electrocardiogram signal. Other biosignals may have specific features known to those skilled in the art.

These effects on the morphology of an electrocardiogram are sometimes subtle and not directly obvious to the human eye. In addition, changes to an electrocardiogram may not correspond to changes in an obvious component of the electrocardiogram waveform (e.g. QRS complex), but may instead correspond to one or more correlations between one or more small and/or apparently unrelated features of the electrocardiogram. In order to provide improved accuracy into analyte concentrations in an individual's blood, in some embodiments, a machine learning model may be applied to predict analyte concentrations from electrocardiogram readings from an individual.

Furthermore, individuals may have different electrocardiogram features. For example, certain persons may have a T wave that is inverted compared to other persons, different average amplitudes of features, slopes of features, or other changes that vary across populations. The correlation between certain features or combinations of features with analyte levels may vary across individuals. Accordingly, simple mathematical models that are built to estimate blood analytes across a population may not be sufficiently accurate for clinical or other use. However, a machine learning model trained with appropriate training samples can identify different features in an electrocardiogram of a subject and estimate or predict blood analyte levels of the subject. In some embodiments a single machine learning model may be capable of determining analyte levels for multiple subjects.

In some embodiments, a machine learning model may be trained on training examples comprising electrocardiogram data of a number of individuals. The training example electrocardiogram data may be taken at or around a time when a target analyte level is known, for example from a blood draw at known times proximate to that of ECG acquisition. For example, in some embodiments, an electrocardiogram may be taken within a 24-hour window or another range of time of one or more associated blood draws. The blood draws and subsequent analysis provide predicted analyte concentrations for a subject at these different times. An estimate of the analyte level may then be generated for the time when the electrocardiogram data was generated. For example, the analyte level at the time an electrocardiogram was taken may be interpolated from one or more analyte measurements taken within a window of time surrounding the electrocardiogram.

In other situations, physiological responses can be used to predict the analyte level in response to a known stimulus. For instance, a pharmacokinetic response can be used to estimate analyte levels of a pharmaceutical in the time following ingestion of a known quantity of pharmaceutical in controlled conditions. Such physiological responses could incorporate multiple parameters: e.g. body weight, blood measurements, urine measurements, metabolic rate, etc. In some embodiments, such responses can be used in conjunction with or in addition to other interpolative estimations.

While training the machine learning model can be performed with a number of techniques, as further discussed below, generally the electrocardiogram data will be input with labeled analyte levels. Depending on the type of machine learning model, the training electrocardiogram data may then be processed by a set of mathematical operations (e.g. addition, multiplication, convolution) involving weight matrices in a number of layers of the machine learning model. After processing, the machine learning model may then generate an output or prediction. The output or prediction is compared to the label (e.g., known blood analyte concentration) for the training data, the machine learning model may be updated, e.g., weight matrices may be updated using back propagation so that the final output of the model better approximates the correct label, or known data, during a next processing stage. The process is continued with additional training data or repeated with the same training data until the model converges.

In some embodiments, the electrocardiogram data associated with subjects in the training data may be read by an electrocardiogram sensor as a number of samples. These samples may be digitized for input to the machine learning model during both training and application. For example, the electrocardiogram may represent data read in over a period of time. In some embodiments, the electrocardiogram may operate at approximately 300 hertz, 60 hertz, 1000 hertz, or at another frequency of sampling to provide accurate data for the electrocardiogram. The electrocardiogram data may be read into the machine learning model in intervals of time. For example, the electrocardiogram data may be used as a 10 second input of data. In some embodiments, rather than a continuous string of data, an average heartbeat may be determined by detecting each heartbeat present in the electrocardiogram signal, aligning each heartbeat based on a common feature such as the R-wave, and averaging each beat to produce an average amplitude at different parts of the beat. This may reduce noise or signal artifact present in the electrocardiogram recording.

The process of training the machine learning model may be repeated for each electrocardiogram in the training data. For example, the training may be performed by inputting each electrocardiogram with a labeled analyte level into the machine learning model. The model may then be updated based on the difference between output prediction of the machine learning model and the correct output (label), e.g., weight matrices are updated. The process may be repeated through all the electrocardiogram data multiple times until the outputs of the machine learning model are within a threshold of accuracy. For example, the threshold may be set to be within a set amount of the estimated analyte values for each electrocardiogram. The threshold may also be set such that it is within a threshold of a measured value at least for a threshold number of electrocardiogram.

While various machine learning models may be used, in some embodiments a convolutional neural net, a recurrent neural net, or a combination of a convolutional neural net and a recurrent neural net may be used. For example, a machine learning model may include 4 convolutional layer and 2 fully connected layers. In some embodiments, fewer or additional layers of different types may also be used. Furthermore, in some embodiments, drop out regularization, skip connections, max pooling, or other techniques may be used.

In an example, a neural net for determining potassium concentrations contains 11 convolutional layers and one final fully connected layer. The first convolutional layer operates on the ECG signal (one or more leads) and contains 64 filters, each with a width of 16. Subsequent layers contain 32 filters each with a width of 16. The stride of the filters for layers 1, 2, 4, 6, 8, and 10 is one, and the stride of the filters for odd layers from 3 to 11 is two. Dropout is implemented between all layers except the first two. Max pooling is implemented after layers 3, 5, 7, and 9. There are skip connections between layers 3 and 6, 5 and 8, 7 and 10, and 9 and the fully connected layer. Batch normalization is implemented between layers 3 and 4, 5 and 6, 7 and 8, 9 and 10, and 11 and the fully connected layer. The convolutional layers use the standard rectified linear unit non-linearity, and the final fully connected layer has no non-linearity. In some embodiments, other machine learning models can include fewer or additional layers, different dropout, max pooling, normalization, or other feature implementation, different numbers and sizes of filters, or changes to other parameters of the machine learning models.

After training, a subject's ECG data may be input into the machine learning model that will predict the subject's analyte concentrations. For example, after training over a population of training data as described herein a subject may use a simple noninvasive electrocardiogram reading to determine an analyte blood concentration level. In some embodiments, the electrocardiogram may be applied as an input to the machine learning model in the same or similar manner as during training. For example, if ten second intervals of electrocardiogram data were used to train a machine learning system, the same type of electrocardiogram data may be input to the machine learning model to predict an analyte level of the subject. Similarly, if an average heartbeat was used over an interval for the training data, the same average heartbeat pre-processing may be applied to the data input into the trained machine learning model.

In some embodiments, training of a machine learning model may be performed at a computer or server capable of large amounts of data processing. For example, a computing or server system may be used to train a machine learning model based on labeled electrocardiogram data. In some embodiments, after training, a machine learning model may be applied by a different computer system than used for training. For example, a computing system or server system may be used to train a machine learning model for an individual, however, after training, the machine learning model may be transferred to and used by an individual's personal computer, mobile device, smart phone, wearable computing device (e.g., smart watch or health band), or the like, where input data is supplied to the trained model via the personal computer, smart watch or wearable computing device. Of course, in some implementations, different servers, computer systems, personal computers, mobile devices, or the like may be used to perform any tasks as described herein, e.g., a distributed network.

In some embodiments, the training data may include hundreds, thousands, tens of thousands, millions, or other quantity of electrocardiogram data and associated blood analyte levels used to label the ECG data. Within the number of training samples, some of the blood analyte levels or electrocardiogram data may not be sufficiently accurate for labeling. For example, some blood analyte measurements may have a high error rate that reduces the certainty of labeling example electrocardiogram data based on the measurements. Accordingly, processing the electrocardiogram data to identify and filter potentially inaccurate measurements in the training data may improve the training of the machine learning model.

Figure 7:
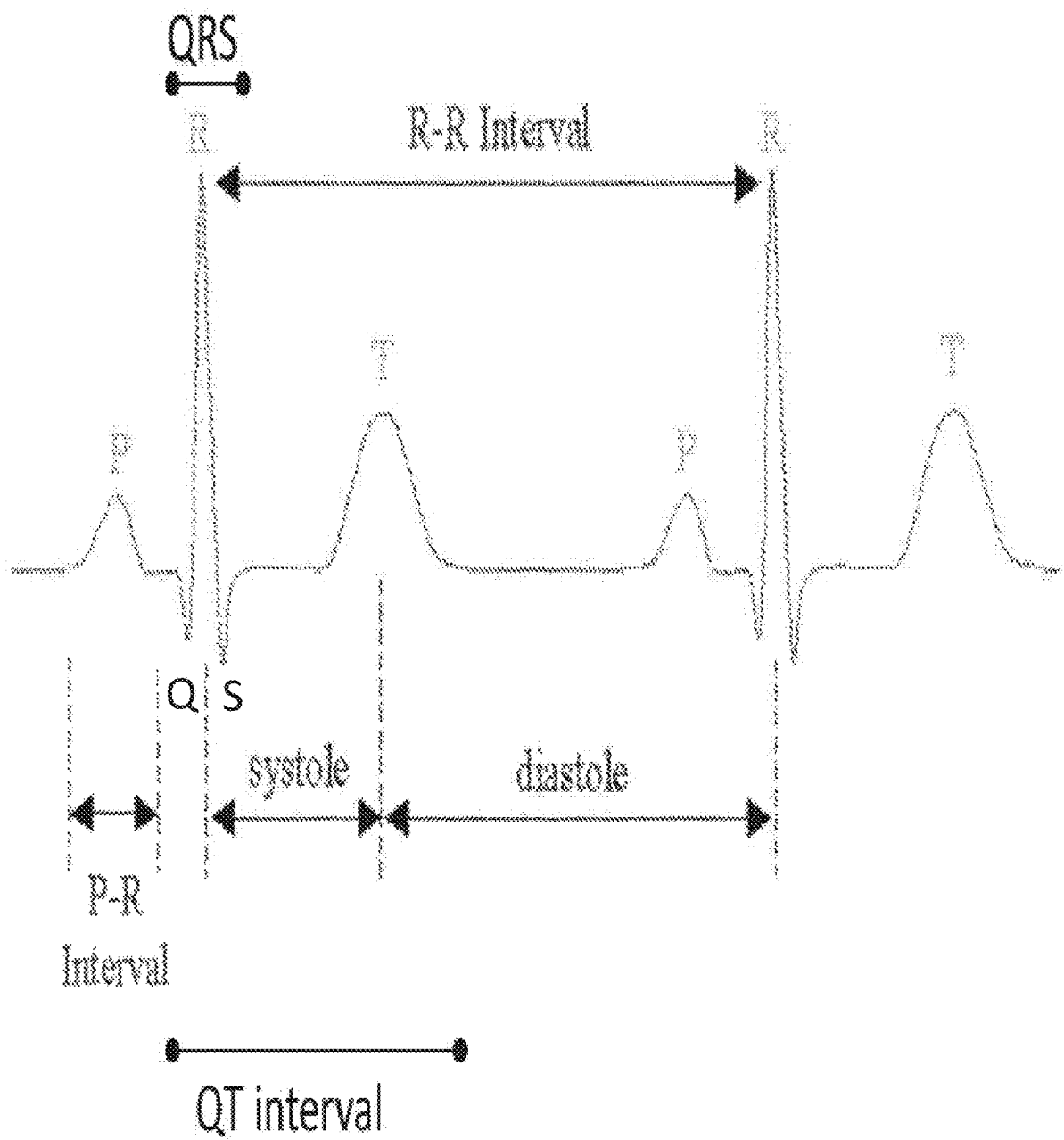
FIG. 7 illustrates example electrocardiogram signals, according to aspects of the disclosure.

For reference, FIG. 7 shows a general electrocardiogram having standard features. For example, the electrocardiogram shows two measured beats. Each beat has a P-wave, a QRS complex, and a T-wave. Each segment has different amplitudes and slopes at various points. As shown, the R-R interval shows the length between peaks of the beats. The electrocardiogram also shows other intervals including a P-R interval, a systole period, a diastole period and a QT interval. Although the elements of these features may be built in to the machine learning model, they are not necessarily individually analyzed by the model. For example, the machine learning model may learn features of relations between features during training that are different than those shown. Furthermore, as discussed above, certain individual's may have different features than shown in a typical electrocardiogram. For example, some individuals may not have a T-wave, may have a bi-phasic T-wave, an inverted T-wave or other features. Accordingly, although described as learning features indicating an analyte level for an individual, such learning should not be attributed to any specific features of an individual's electrocardiogram.

FIG. 1 illustrates an example analyte measurement system 100 that supports the analysis of electrocardiograms or other biosignals as described herein. The analyte measurement system 100 may include an analyte analysis system 110 and a machine learning training system 150. Although shown as separate components, in some embodiments, the analyte analysis system 100 and the machine learning training system 150 may be part of the same computer system. In some embodiments, the analyte analysis system 110 and the machine learning training system 150 may be remote components connected over a network. For example, the analyte analysis system 110 may be located on a personal device such as a mobile device, personal computer, smart watch or wearable fitness band (collectively "wearable computing device"), or the like. The machine learning training system may be located on the same device as the analyte analysis system 110 or on a remote device such as a central server.

In some embodiments, there may be fewer or additional components than shown in FIG. 1. For example, in some embodiments there may be additional analyte analysis systems 110. Accordingly, additional analyte analysis systems may be used for providing analyte predictions for a number of different subjects. For example, a machine learning model 125 may be provided to a number of analyte analysis systems at different computing devices to provide predictions of analyte concentrations at different locations and for different subjects. Furthermore, while an electrocardiogram sensor 115 is shown as part of analyte analysis system 100, in some embodiments, there may be different electrocardiogram sensors (not shown) that are used in different parts of training and application stages of a machine learning model.

The machine learning training system 150 may include model training service 160 electrocardiogram training data 155, machine learning model 125, and data labeling service 165. The electrocardiogram data 155 includes electrocardiograms taken from a number of subjects in a population. The electrocardiograms may include a segment of an electrocardiogram for each subject, e.g., a representation of 10 seconds, 30 seconds, 5 seconds, or another length of time of an electrocardiogram. Electrocardiogram training data 155 also includes one or more analyte levels associated with each electrocardiogram stored in the data, where such levels may be used to label the associated ECG data. For example, an electrocardiogram segment taken at a first time may be from an individual that had one or more blood draws during a surrounding time period. The blood draws can be taken within a window of time of the electrocardiogram segment such that they provide some indication of an analyte level at the time of the electrocardiogram. Accordingly, each of the blood draws and the electrocardiogram segment may have a time stamp indicating when they were taken. In some embodiments, the electrocardiogram training data 155 may include additional data associated with individuals from which the ECG data was obtained. For example, the electrocardiogram training data 155 may include height, weight, sex, race, health conditions, or other data about subjects associated with an electrocardiogram.

In some embodiments, raw electrocardiograms and blood analyte levels in the electrocardiogram training data 155 may be processed by a data labeling service 165. The data labeling service 165 may determine labels for each electrocardiogram in electrocardiogram training data 155 based on estimated analyte levels at the time each electrocardiogram was taken. For example, the data labeling service 165 may label each electrocardiogram with a classification. In some embodiments, a classification may be whether or not an analyte level is high. While some description herein focuses on labeling electrocardiograms as high, in various embodiments additional classifications could be used as labels. For example, the data labeling service may label each electrocardiogram as high, medium, or low. In some embodiments, additional labels may be used as well as direct estimations of a blood analyte level. For example, data labeling service 165 may determine an estimated blood analyte level and may also provide an estimated error or confidence associated with the estimated level, as described herein.

In order to label electrocardiogram training data 155, data labeling service 165 may analyze each electrocardiogram and associated analyte levels individually. For example, the data labeling service 165 may determine whether there are multiple high analyte level measurements within a certain time frame of the electrocardiogram. In some embodiments, the data labeling service 165 may determine a regression line that fits to measured analyte levels. The value of the regression line at the time of the electrocardiogram may be used to determine an estimated analyte level and determine whether to label the electrocardiogram with a particular classifier. In some embodiments, the data labeling service 165 may also determine a statistical measure (e.g. r-squared value) of the fit of a regression line to the analyte measurements. This measure may be used to determine a confidence level for the estimated analyte level at the time of the electrocardiogram. In some embodiments, the data labeling service 165 may remove or filter some electrocardiograms from electrocardiogram training data 155 if an estimated analyte level does not have a high enough level of certainty.

In some embodiments, the data labeling service 165 may use other statistical estimation techniques to determine estimated analyte levels at the time of an electrocardiogram. For example, the data labeling service 165 may use a GPR analysis to determine how to label data. In the GPR analysis, the data labeling service 165 may take each of the analyte measurements associated with an electrocardiogram and determine an error for each of the measurements. In some embodiments, the error may be based on data provided with the blood analyte measurements (e.g. from a lab or technician), based on known accuracy of measured analytes, based on errors associated with measurements at different times of day, or a standard error range provided to each of the measurements. For example, for certain applications, the data labeling service 165 may use an estimated error 1%, 3%, 5%, 10% or another error range.

The GPR analysis may also assume a predicted range for the rate of change for an analyte level. Accordingly, the further from the point of time of a measured analyte level, the larger the potential range of an estimated analyte level based on the original error range and the potential change in analyte level over time. By using several measurements over time, the GPR analysis may estimate an analyte measurement at the time of the electrocardiogram and a confidence interval of that estimation. For example, the confidence interval may represent a range where the GPR analysis determines there is a threshold percentage chance that an analyte level is within that range. The confidence interval may be set at 85%, 95%, 99.7% or another level indicating a sufficient level of confidence that the analyte level is within the estimated range. Example calculations of a GPR analysis as applied to analyte levels over time are provided in FIGS. 2A-2D.

The data labeling service 165 may use the output of the GPR analysis to determine a label for each electrocardiogram. For example, if the data labeling service 165 determines an estimated analyte level for an electrocardiogram that is above a threshold value, the data labeling service 165 can label the electrocardiogram with a high analyte label. In some embodiments, the data labeling service 165 may only label an electrocardiogram with a high analyte level if the entire confidence interval is above the threshold level. The data labeling service 165 may also label an electrocardiogram with a particular label such as high, and provide a certainty label by determining the likelihood that the analyte level is over a threshold for high analyte levels. The certainty level may be used when training a machine learning model 125 with the electrocardiogram training data 155. In some embodiments, the data labeling service may also remove certain electrocardiograms from electrocardiogram training data 155 in response to determining that a confidence interval is too large or the confidence interval doesn't provide a sufficient certainty that the analyte level at the time of the electrocardiogram is at a particular threshold.

After processing by the data labeling service 165, electrocardiogram training data 155 may be provided as labeled to a model training service 160 to train the machine learning model 125. In some embodiments, multiple electrocardiogram waveforms are averaged to form a single averaged waveform that serves as the input for the model training service 160. For example, the electrocardiogram training data 155 may be pre-processed to form a set of inputs with labeled data for the model training service. Each of the inputs may be an averaged waveform of heartbeats located within a set interval of electrocardiogram data. In some embodiments, the electrocardiogram data may be stored over a complete waveform interval. However, in some embodiments, additional pre-processing may be performed such as smoothing, noise reduction, or other processing. It should be understood, however, that any recording length as well as any other lead or combination of leads selected from leads I, II, III, aVR, aVL, aVF, V1, V2, V3, V4, V5, and V6 are suitable for use as inputs to model training service 160.

The machine learning model 125 may start as a generic machine learning model. For example, the machine learning model 125 may start with randomized values for a number of matrices within the model. The machine learning model 125 may be set with a number of convolutional layers, recurrent layers, or the like prior to training by the model training service 160.

In some embodiments, the machine learning model 125 may be a recurrent neural network. A recurrent neural network may receive sequential data as an input, such as consecutive electrocardiogram samples or beats, and then the recurrent neural network updates its internal state at every time step. In some embodiments the machine learning model may be a convolutional neural network. A convolutional neural network may include a number of convolutional layers that apply convolution operations using weight matrices and non-linearities to identify one or more features in the input data. The output of each convolutional layer may then be passed up to another layer to provide further analysis. In some embodiments, the machine learning model 125 may have a combination of recurrent and convolutional layers that identify and quantify different features in input data.

The model training service 160 may train a model based on each of the labeled electrocardiograms in the electrocardiogram training data 155. In some embodiments, the model training service 160 uses automatic statistical analysis of labeled data in order to determine which features to extract and/or analyze from a sensed biosignal (e.g. an electrocardiogram). The model training service 160 may determine which features to extract and/or analyze from an electrocardiogram based on labeled electrocardiogram training data 155 that it receives.

In some embodiments, the model training service 160 may be configured to receive a certain length of raw electrocardiogram data as an input. For example, an input to the model training service 160 may be 10 seconds or more of an electrocardiogram signal from lead I of an electrocardiogram sensor 115. In some embodiments the model training service 160 may use the untrained machine learning model 125 as a function approximator, mapping a high dimensional input (the raw electrocardiogram waveform) into a classification for the data (e.g. whether an analyte value is high). In some embodiments, the machine learning model may provide direct approximation of an analyte level. Based on differences between the classification generated or number generated by the machine learning model 125, the model training service 160 may update the machine learning model to better fit the labeled data.

In some embodiments, the machine learning model 125 may also change how it updates the machine learning model based on one or more labels of the electrocardiogram training data 155. For example, if an electrocardiogram is provided with a certainty level associated with the label, the model training service 160 may modify the amount values in weight matrices of the machine learning model 125 are changed based on the certainty. For example, if an electrocardiogram has a certainty of 75% for a label, the 75% certainty may be used to reduce a penalty for the machine learning model 125 for incorrectly estimating the label.

The model training service 160 may provide each electrocardiogram in electrocardiogram training data 155 to the machine learning model 125 until the machine learning model 125 predicts the labels with sufficient accuracy. For example, the model training service 160 may determine that the machine learning model 125 is trained if it can predict a threshold number of labels in the electrocardiogram training data 155 correctly. In some embodiments, only part of the electrocardiogram training data 155 may be provided to the model training service 160 to train the machine learning model 125 and the remaining electrocardiogram training data 155 may be stored as a verification set. The model training service 160 may then verify the accuracy of the machine learning model 125 by testing the model on the verification set.

After a machine learning model 125 has be generated and verified, it can be provided to one or more analyte analysis systems 110. For example, as the machine learning model 125 is trained on electrocardiogram training data 155 from across a population of individuals, it can be used on electrocardiograms not stored in electrocardiogram training data 155 or used as training examples, which are input into machine learning model 125 to predict a subject's analyte levels. In some embodiments, the input ECGs to learning model 125 may be used by machine learning training system 150 to retrain a machine learning model 125 to improve the model. As a new machine learning model 125 is generated, it may be pushed as an update to analyte analysis system 110.

The analyte analysis system 110 in FIG. 1 may provide data from an electrocardiogram sensor 115 to store as electrocardiogram data 120. In some embodiments, the electrocardiogram sensor 115 may be separate from the analyte analysis system 110 and may provide an electrocardiogram segment remotely to the analyte analysis system. The electrocardiogram data 120 may then be input to machine learning model 125 by electrocardiogram analyzer 130. The machine learning model 125 may be the same as was trained by machine learning system 150. In some embodiments, the machine learning model 125, the electrocardiogram analyzer 130, or other components of the analyte analysis system 110 may be on a separate computing system than the analyte analysis system 110. For example, the machine learning training system 150 may have one or more components of the analyte analysis system 110.

The electrocardiogram analyzer 130 may apply the machine learning model 125 by inputting a segment of electrocardiogram data 120 to electrocardiogram analyzer 130. As discussed herein, the electrocardiogram data may be pre-processed into set interval segments, average heartbeats, smoothed, noise reduced, or otherwise provided in a set manner to the electrocardiogram analyzer 130. The electrocardiogram analyzer 130 may then input a segment of electrocardiogram data 120 to the machine learning model 125 to generate an output of an analyte concentration or classification. The electrocardiogram data 120 input to the machine learning model 125 may be provided in the same manner as the electrocardiogram training data 155 used to train the model. For example, if the electrocardiogram data 155 was provided as ten second segments, the electrocardiogram analyzer 130 provides a ten second segment of electrocardiogram to the machine learning model 125.

In some embodiments, a user interface generator 135 provides the analyzed data to a user interface. For example, the user interface generator 135 may generate a user interface including one or more of: an analyte output, an electrocardiogram output, additional analyte data, analyte classification, or a combination. For example, in some embodiments, a user interface generator 135 may provide a user interface as described with reference to FIG. 3.

While shown as including a machine learning model 125 for particular analyte analysis, in some embodiments, the analyte analysis system 110 may provide additional data for additional analyte concentration. For example, machine learning training system 150 may provide multiple machine learning models 125 for different analytes based on electrocardiogram training data 155 with different analyte measurements.

In some embodiments, an analyte analysis system 110 includes an alert service 140. The alert service 140 may generate an alert to an individual (e.g., a subject, relative, care giver, or health professional) if the machine learning model 125 provides a classification that an analyte level is high or low. In some embodiments, the machine learning model 125 provides a direct estimation of an analyte level. Then the alert service 140 can provide an alert if an analyte level is above or below a certain threshold. For example, for a potassium serum level, the individual may be alerted if the level is above 5 mEq/L. Furthermore, the alert service 140 may provide additional alerts to other individuals. For example, an alert may be provided to a doctor, a caretaker, a health professional, a significant other, or the like.

Figure 2A:
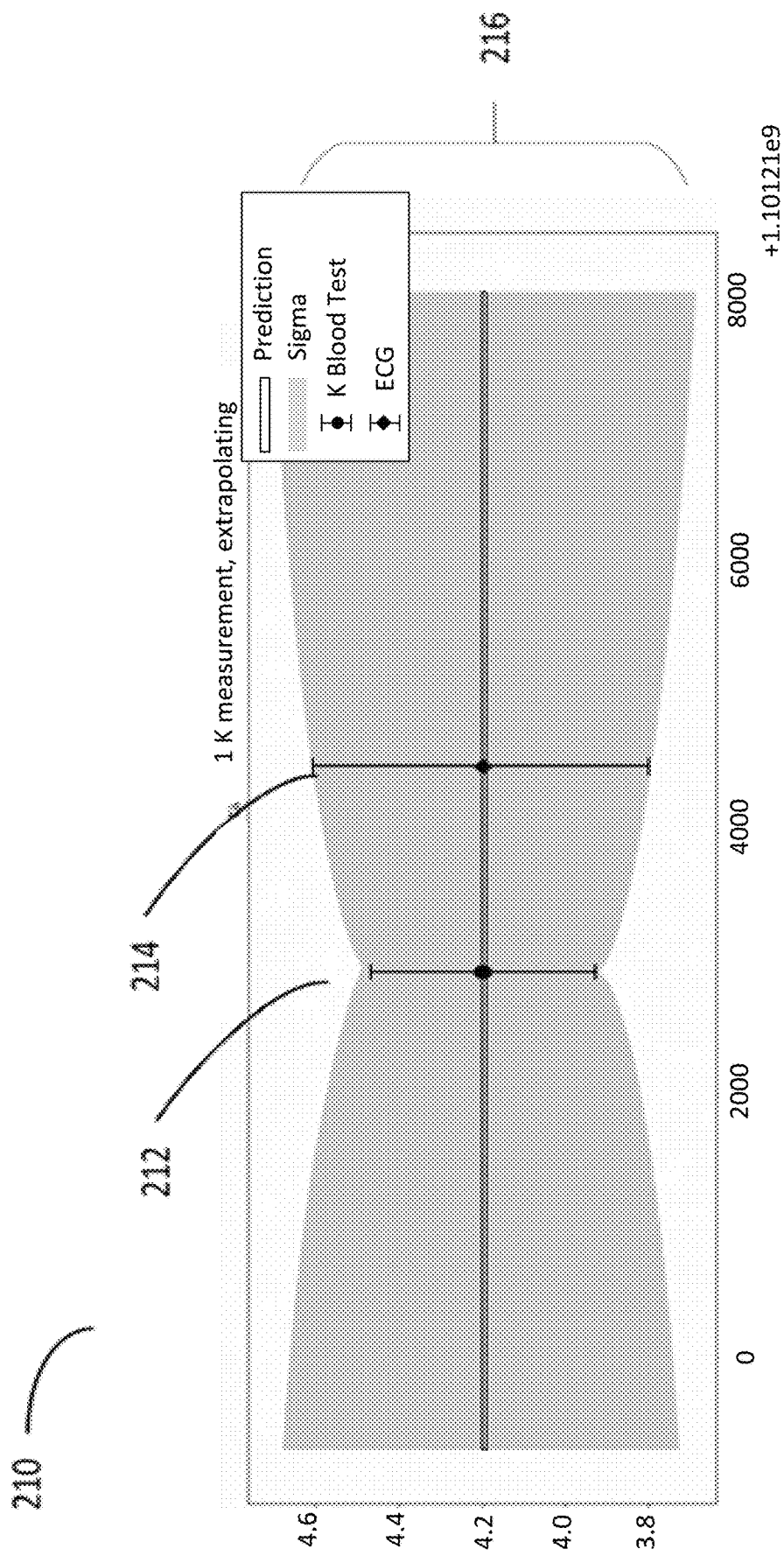
FIG. 2A illustrates an example process used to perform data labeling, according to aspects of the disclosure.
Figure 2B:
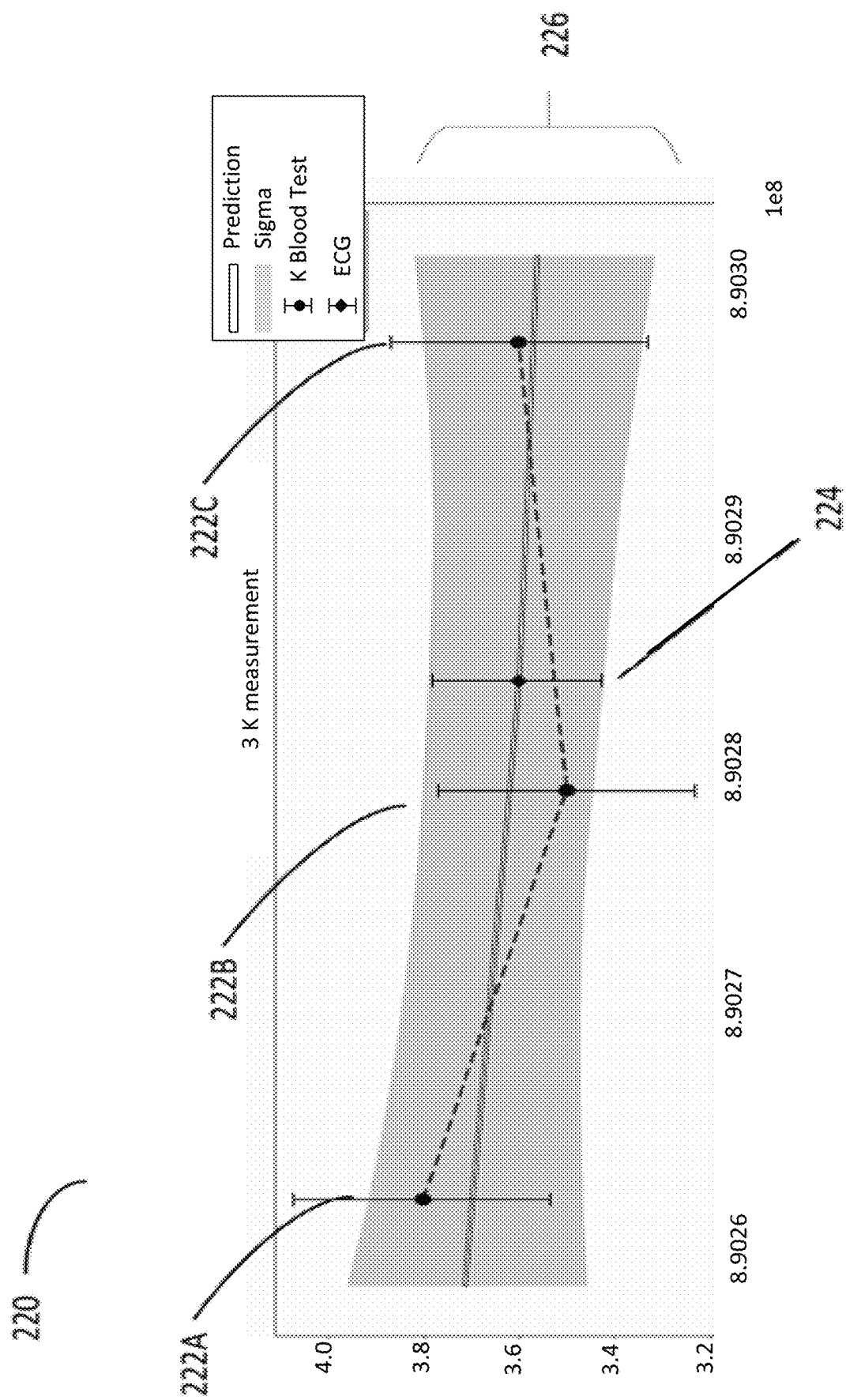
FIG. 2B illustrates an example process used to perform data labeling, according to aspects of the disclosure.
Figure 2C:
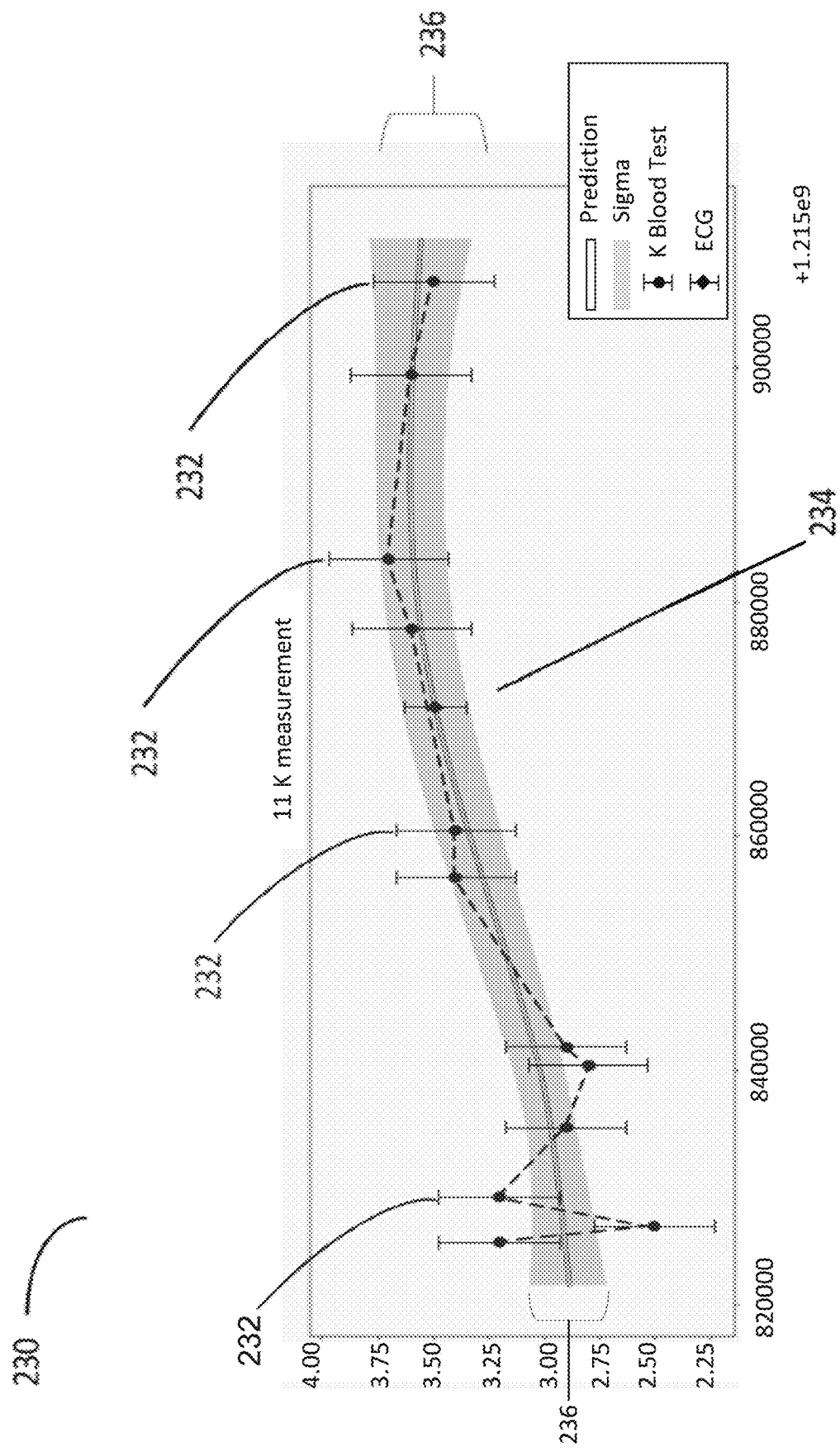
FIG. 2C illustrates an example process used to perform data labeling, according to aspects of the disclosure.

FIGS. 2A-2C show examples of estimated analyte levels over time that are associated with an electrocardiogram in training samples of electrocardiogram data. The estimations show an estimated analyte level and a confidence in that analyte level over time. In some embodiments, the estimated analyte levels may be generated by a data labeling service 165 as described with respect to FIG. 1. The examples shown in FIGS. 2A-2C include measurements of potassium levels and predicted potassium levels generated based on the measurements. The potassium levels are represented in milliEquivalents per liter (mEq/L). For reference, a mEq/L level over 5.0 may be considered a high potassium level known as hyperkalemia. While the charts in FIGS. 2A-2C show examples of potassium levels, in different examples, measurements of other analytes can be used to generate similar estimations of analyte levels at the time an electrocardiogram is taken. Furthermore, the confidence intervals as described with reference below to potassium measurements may also be applied to other estimations based on other signals in different machine learning applications.

Beginning with FIG. 2A, a chart 210 of analyte estimation is shown for a period of time that includes one electrocardiogram 314 and one blood test 312. As can be seen a single analyte measurement 212 is used to estimate an analyte level over the entire time frame. Because there is only one measurement, the estimated analyte level remains unchanged over time. The analyte measurement 212 has an estimated error that is represented by the thickness of the confidence interval 216 at the time of the analyte measurement. For example, in the example of a potassium measurement, the confidence interval may be set at 5%, but other error ranges may be used for other analytes or measurement techniques. Because the analyte level can change over time, the confidence interval 216 increases over time as well. For example, in some embodiments, the range may be increased by the square root of the time elapsed since the measurement. Accordingly, the confidence interval is larger at the time of an electrocardiogram 214 than it is at the time of the analyte measurement 212. As described above, the estimated analyte level at time 214 and the confidence interval can be used together to train a machine learning model.

The chart 220 in FIG. 2B shows improved confidence in analyte level with the addition of multiple analyte measurements. As shown in chart 220, there are three analyte measurements 220A, 220B, and 220C. Each of the measurements 220A, 220B, and 220C includes an estimated value of the analyte level as well as an error range. The error range may be increased over time based on a rate of change physiologically possible for a particular analyte. In other machine learning applications, the potential rate of change may be set based on other physical properties of the system. The GPR analysis generates an estimated analyte level over the time as well as a confidence interval 226. Taking the confidence interval 226 as it is calculated at the time of the electrocardiogram 224 provides an estimated range of the analyte level that corresponds in time to the electrocardiogram measurement. As described above, the estimated analyte level at the time of electrocardiogram 224 can be used to train a machine learning model. In some embodiments, the confidence interval may also be used by a data labeling service or a model training service, as described herein, to further improve training of the machine learning model.

FIG. 2C shows another example chart 230 that includes a measurement of electrocardiogram 234 and 12 analyte measurements 232. The additional analyte measurements can improve the size of a confidence interval 236. For example, while the confidence interval 216 shown in FIG. 2A may be approximately 0.8 mEq/L, the confidence interval in chart 230 shown in FIG. 2C is approximately 0.25 mEq/L. Providing more blood analyte measurements may not necessarily provide a better confidence interval, however, the GPR analysis determines the levels based on the consistency of measurements and proximity in time to the electrocardiogram measurement. Accordingly, regardless of the number of analyte measurements, the process can be used by a data labeling service to determine an appropriate estimated analyte level and the certainty of the estimate for filtering or labeling data to train a machine learning model.

Based on the value of an estimated analyte level and a confidence interval, a data labeling service can characterize different training data. For example, in the context of potassium levels, the data labeling service may characterize each sample in the training data as high, normal, or uncertain. Those data samples that are determined to be uncertain may be excluded from the training data. Those that are characterized as high or normal may be labeled as such for use training the machine learning model. In some embodiments, the confidence interval may also be used to determine a penalty amount based on the certainty that a sample is accurately labeled as high or normal. In other machine learning systems, confidence levels may be used to label data for additional or alternative characterizations other than high or low.

Figure 3:
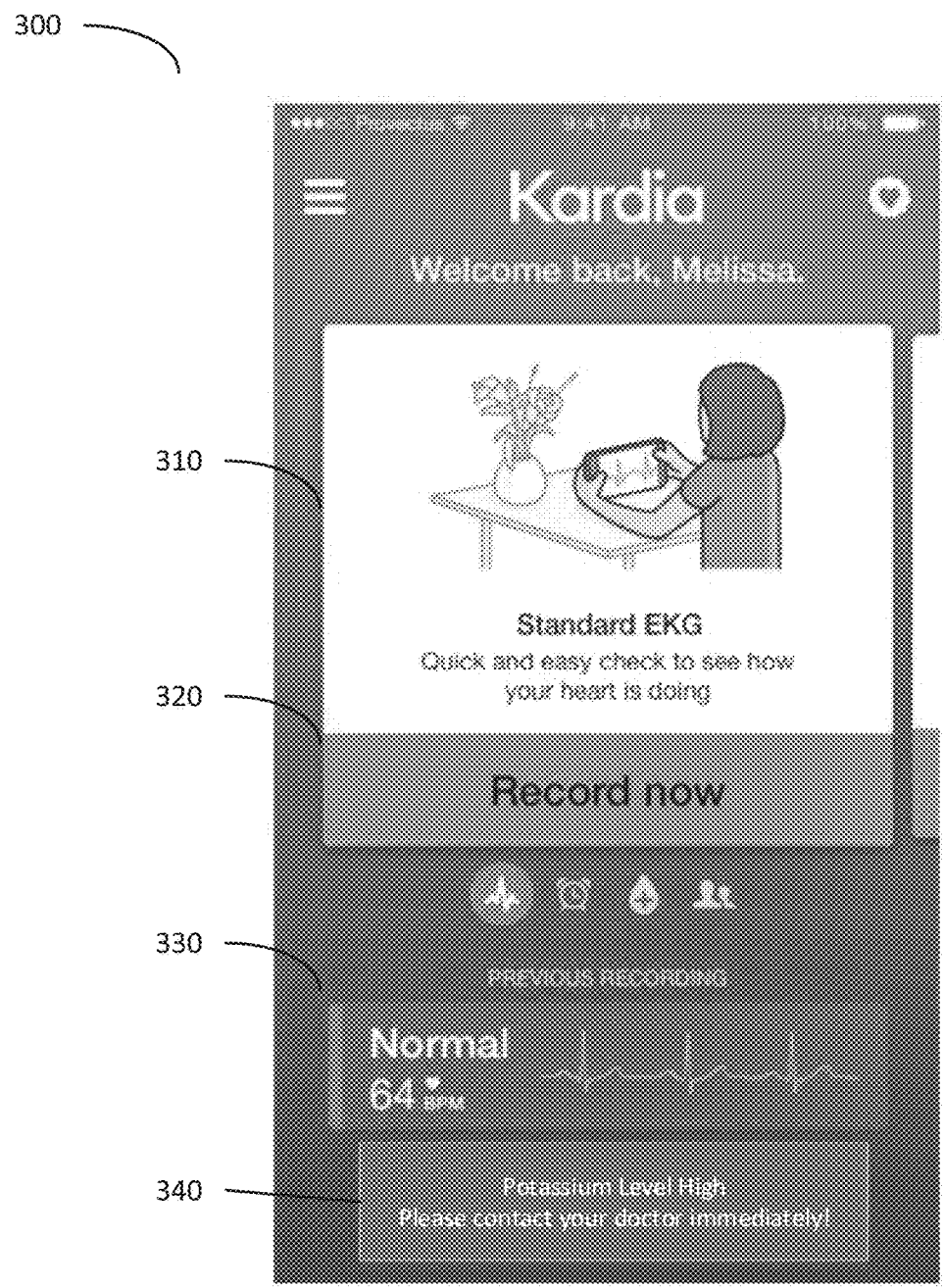
FIG. 3 illustrates an example user interface as generated by an analyte measurement system as discussed herein, according to aspects of the disclosure.

FIG. 3 depicts an example user interface 300 showing an analyte analysis system as described herein. For example, in some embodiments the user interface 300 may be generated by user interface generator 135 as described in FIG. 1. The user interface 300, or variants thereof, may be displayed on a mobile device, a personal computer, a web browser, a smart watch, or other computing devices.

The user interface 300 includes an interface 310 prompting a user to perform a standard electrocardiogram. The user may have an option 320 to record the electrocardiogram when an electrocardiogram sensor is in place. The electrocardiogram 330 may be displayed as it is recorded by the individual. Furthermore, an output 340 of an analyte level of the individual may be provided. In some embodiments, the user interface 300 may not provide an output unless the machine learning model outputs a classifier that the analyte level is above or below a threshold. In some implementations, the electrocardiogram sensor may pass data to an electrocardiogram analyzer as input to a machine learning model as described above with respect to FIG. 1. In some embodiments, the electrocardiogram sensor may pass data as input to a number of machine learning models to test levels of additional or multiple analytes.

In some embodiments, a user interface generator may generate an additional user interface element 340 that provides an estimate of the analyte level. In some embodiments, a user interface generator may provide the analyte levels regardless of their range. An alert service may use the data provided by the machine learning model to determine whether to alert the individual to additional issues with potential analyte levels. For example, as shown in user interface element 340, in some embodiments, a user interface may provide an alert and a recommendation to contact a doctor or physician or may also send the alert to others such as a medical professional or loved one. In some embodiments, an alert service may request a retest of an electrocardiogram prior to providing an alert to contact a doctor or physician.

Figure 4:
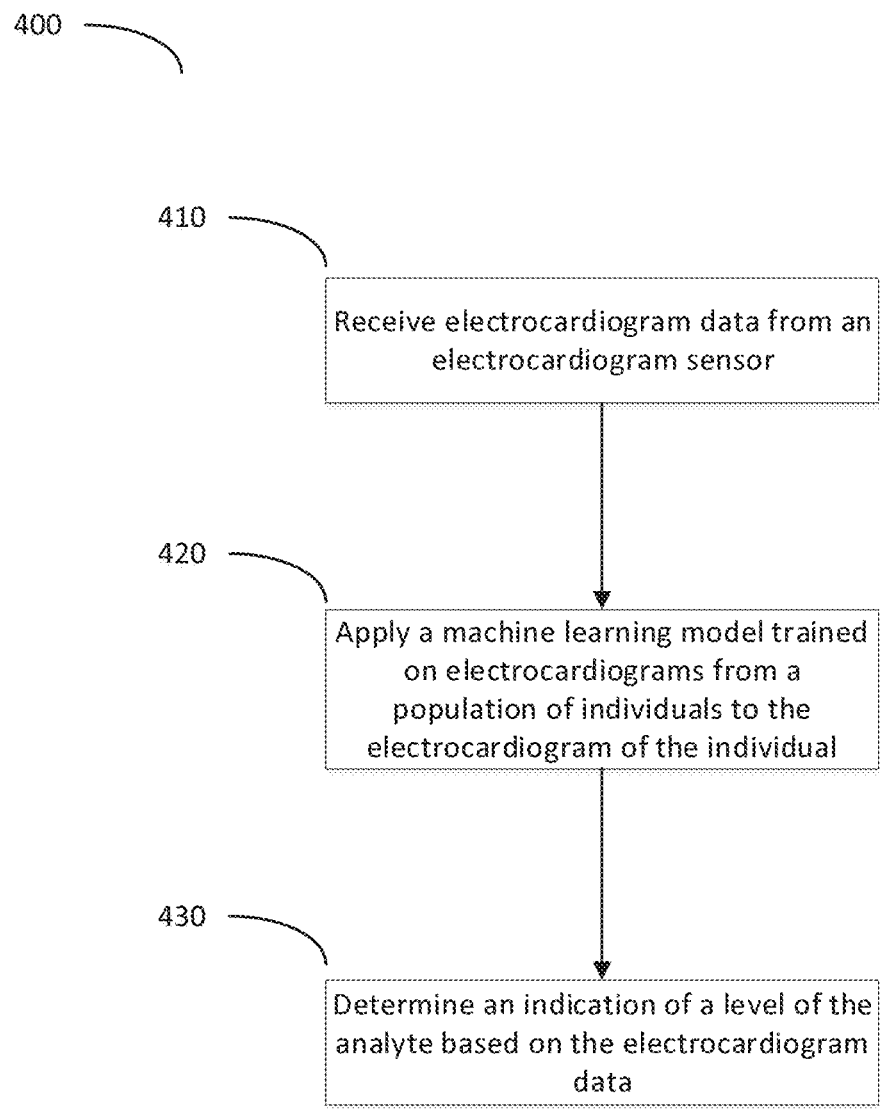
FIG. 4 illustrates flow diagram of processes as performed by an analyte measurement system, according to aspects of the disclosure.

FIG. 4 depicts a data flow 400 illustrating the application of a machine learning model to an electrocardiogram of a subject. In some embodiments, the processes described with respect to FIG. 4 may be performed by one or more components of the analyte measurement system 100 as described with reference to FIG. 1.

Beginning in block 410, an analyte measurement system may receive electrocardiogram data from an electrocardiogram sensor. For example, the electrocardiogram sensor may provide real-time data of an individual's heartbeats. In some embodiments, the electrocardiogram sensor may be a 1 lead sensor, a 2 lead sensor, a 3 lead sensor, a 4 lead sensor, a 6 lead sensor, or a 12 lead sensor. In some embodiments, the analyte measurement sensor may utilize only a subset of the electrocardiogram data that is received.

In block 420, the analyte measurement system may apply a machine learning model to the electrocardiogram of the subject. In some embodiments, the machine learning model has been trained based on previous electrocardiogram training samples of a population of subjects having one or more associated analyte measurements. Accordingly, the machine learning model may be trained on electrocardiograms that have associated estimates of a blood analyte level, as described above.

In block 430, the analyte measurement system may determine an indication of a level of the analyte based on the electrocardiogram data. For example, the analyte measurement system may classify the electrocardiogram data as high based on its analysis. In some embodiments, the analyte measurements system may determine a specific predicted level of the individuals analyte level based on the electrocardiogram data.

Figure 5:
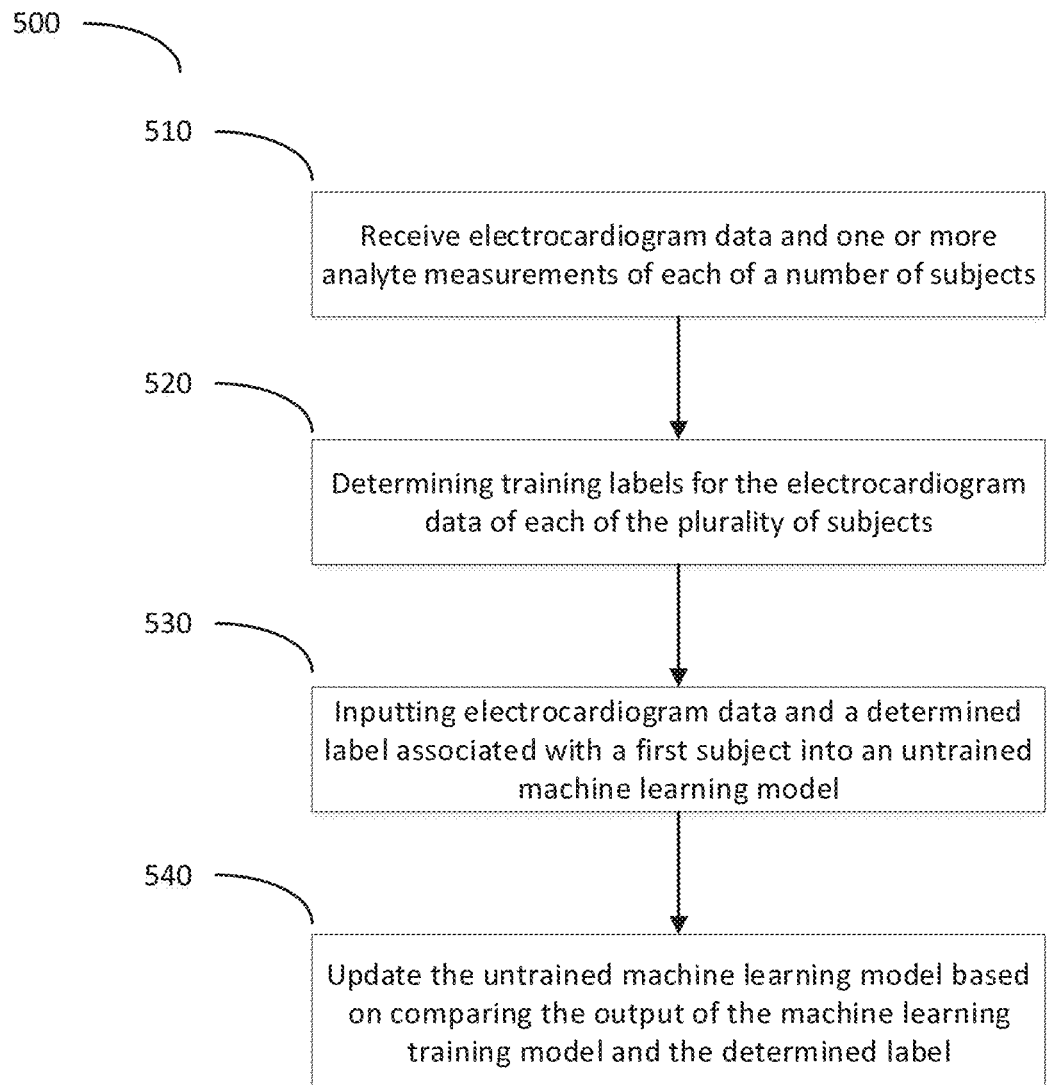
FIG. 5 illustrates flow diagram of processes as performed by an analyte measurement system, according to aspects of the disclosure.

FIG. 5 depicts a data flow 500 illustrating training of a machine learning model using electrocardiogram data training samples of tested subjects. In some embodiments, the processes described with respect to FIG. 5 may be performed by one or more components of the analyte measurement system 100 as described with reference to FIG. 1.

Beginning in block 510, an analyte measurement system may receive electrocardiogram data and one or more analyte measurements of each of a number of subjects. For example, the data may be aggregated from patients in a doctor's office or hospital, from research subjects, or from other sources. In some embodiments, the electrocardiogram data may include a segment of recorded electrocardiogram data taken at a different time than the one or more analyte measurements. Furthermore, some subjects may have different numbers of analyte measurements associated with their electrocardiogram data than others.

In block 520, the analyte measurements system may determine training labels for the electrocardiogram data of each of the subjects. For example, a data labeling service 165 as described with reference to FIG. 1 may label or filter electrocardiogram data. For example, labeling may be performed based on estimating an analyte level and determining if it is over a threshold. In some embodiments, the analyte measurement system may perform a GPR analysis (or other regression process) to determine an estimated analyte level and an indication of estimated error. In some embodiments the analyte measurement system may label electrocardiograms as one of multiple classifications, an estimated value of an analyte, or another label. The label may also include one or more indication of the certainty of the label. An analyte measurement system may also remove or filter certain electrocardiograms from the set of training data based on uncertainty associated with the labels.

In block 530, the analyte measurement system may input electrocardiogram data of a subject, along with a determined label, into a machine learning model to train that model. For example, an interval of the electrocardiogram data for a subject may be provided to the machine learning model. The machine learning model then processes the data to generate an output.

In block 540, the analyte measurement system can update the machine learning model based on comparing the output of the machine learning training model and the determined label. For example, if the subject's electrocardiogram data was labeled with a classification of a high analyte level and the machine learning model returns an output of a normal analyte level, then the machine learning model may be updated by updating weights of matrices in one or more layers of the machine learning model.

The processes in blocks 530 and 540 may be repeated with each of the labeled electrocardiogram data of the subjects. The process may continue to train the model for a set amount of time or cycles of inputting all the labeled electrocardiogram data. In some embodiments the machine learning model may be trained until has an accuracy level over a certain amount. After the machine learning model is trained, it may be used to test electrocardiograms received from new subjects to predict approximate blood analyte levels, high or low analyte levels, or the like.

Figure 6:
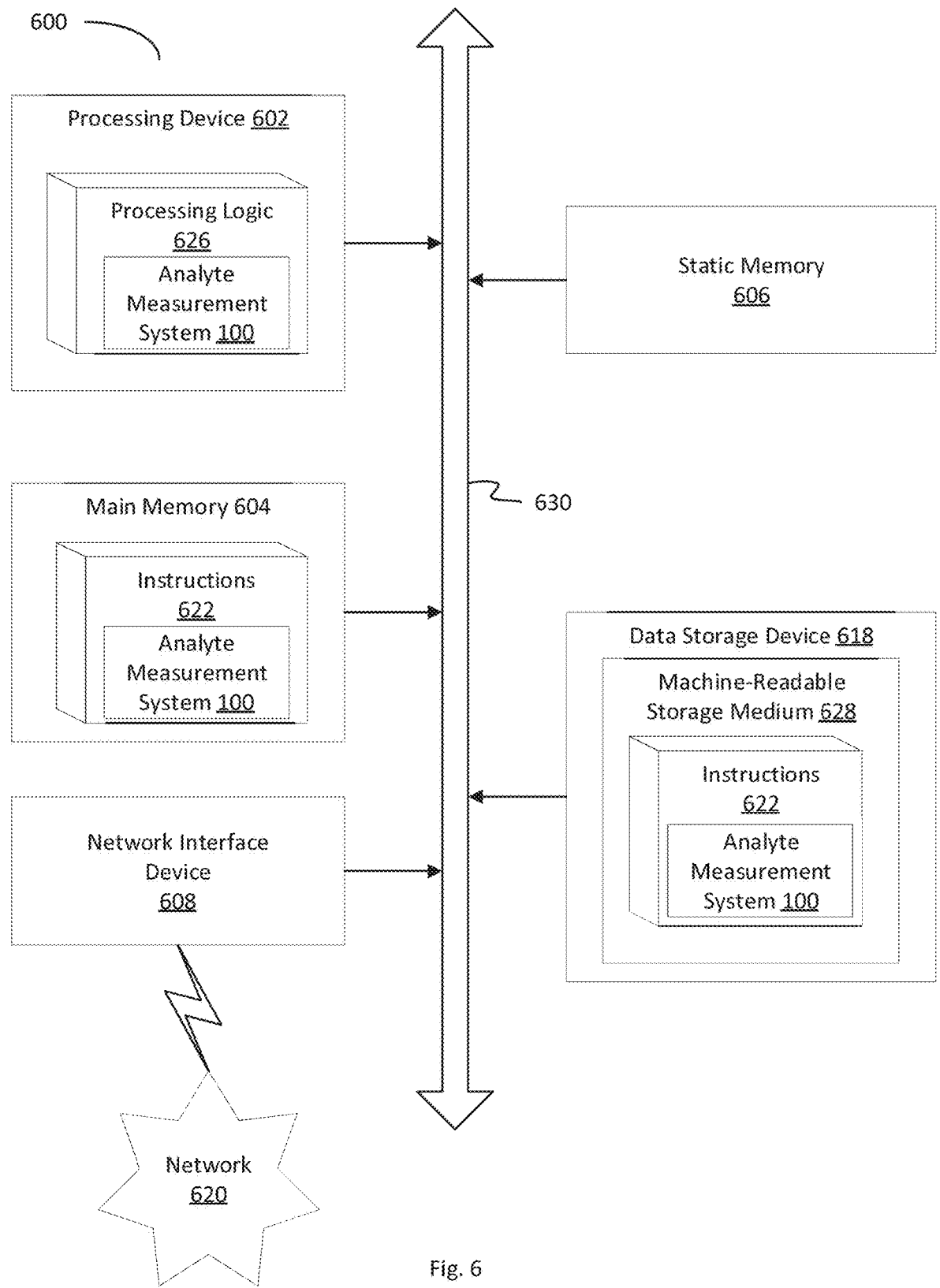
FIG. 6 illustrates an example computing environment of an analyte measurement system, according to aspects of the disclosure.

FIG. 6 illustrates a diagrammatic representation of a machine in the example from of a computer system 600 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, wearable computing device, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 600 may be representative of a server, such as one or more components of analyte measurement system 100 configured to perform processes as described above.

The exemplary computer system 600 includes a processing device 602, a main memory 604 (e.g., read-only memory (ROM), flash memory, dynamic random access memory (DRAM), a static memory 606 (e.g., flash memory, static random access memory (SRAM), etc.), and a data storage device 618, which communicate with each other via a bus 630. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 602 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute processing logic 626, which may be one example of system 400 shown in FIG. 4, for performing the operations and steps discussed herein.

The data storage device 618 may include a machine-readable storage medium 628, on which is stored one or more set of instructions 622 (e.g., software) embodying any one or more of the methodologies of functions described herein, including instructions to cause the processing device 602 to execute analyte measurement systems 100. The instructions 622 may also reside, completely or at least partially, within the main memory 604 or within the processing device 602 during execution thereof by the computer system 600; the main memory 604 and the processing device 602 also constituting machine-readable storage media. The instructions 622 may further be transmitted or received over a network 620 via the network interface device 608.

The machine-readable storage medium 628 may also be used to store instructions to perform a method for analyte measurement systems, as described herein. While the machine-readable storage medium 628 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:

1. A system for non-invasively predicting a level of an analyte comprising:
    an electrocardiogram sensor; and
    a processing device operatively coupled to the electrocardiogram sensor, wherein the processing device is to:
        analyze electrocardiogram training data comprising an electrocardiogram of each of a plurality of subjects and one or more measured analyte levels associated with each electrocardiogram to determine an associated label for each electrocardiogram of the electrocardiogram training data, the associated label for each electrocardiogram of the electrocardiogram training data based on a regression line fitted to the one or more measured analyte levels associated with each electrocardiogram, wherein the associated label is determined from the regression line at a time of measurement of the associated electrocardiogram;
        train a machine learning model by:
            analyzing each electrocardiogram of the electrocardiogram training data to generate an output; and
            comparing the output generated for each electrocardiogram of the electrocardiogram training data to the associated label for each electrocardiogram of the electrocardiogram training data to update the machine learning model using backpropagation, wherein one or more weight matrices of the machine learning model are adjusted based on a confidence interval associated with the associated label for each electrocardiogram of the electrocardiogram training data;
        receive electrocardiogram data of a subject from the electrocardiogram sensor; and
        apply the machine learning model to the received electrocardiogram data to determine an indication of a measured analyte level of the subject based on the electrocardiogram data.

2. The system of claim 1, wherein the received electrocardiogram data comprises an electrocardiogram signal measured over multiple heartbeats of the subject.

3. The system of claim 2, wherein applying the machine learning model comprises pre-processing the electrocardiogram signal to generate an average heartbeat over the multiple heartbeats of the subject.

4. The system of claim 1, wherein the electrocardiogram sensor comprises a 2 lead or 3 lead electrocardiogram sensor.

5. The system of claim 1, wherein the machine learning model is one of a convolutional neural network, a recurrent neural network, or a combination of a convolutional and a recurrent neural network.

6. The system of claim 1, wherein the analyte is one of potassium, magnesium, or calcium.

7. The system of claim 1, wherein the indication of the measured level of the analyte indicates one of an estimate of concentrations of the measured analyte in the subject or an indication of a classification of the measured analyte level as high or normal.

8. The system of claim 1, wherein the processing device is part of a mobile device comprising a display screen, and wherein the processing device is further to cause the display screen to display the indication of the level of the analyte on the display screen.

9. A method, comprising:
    receiving, by a processing device, electrocardiogram training data comprising a plurality of electrocardiograms and one or more analyte measurements associated with each of the electrocardiograms;

determining, by the processing device, training labels for the plurality of electrocardiograms of the electrocardiogram training data based at least in part on a regression line fitted to the one or more analyte measurements associated with each of the electrocardiograms, wherein the training labels are determined from the regression line at a time of measurement of the associated electrocardiogram of the plurality of electrocardiograms;

training a machine learning model by:
  analyzing each electrocardiogram of the electrocardiogram training data to generate an output; and
  comparing, by the processing device, the output generated for each electrocardiogram of the electrocardiogram training data to the associated label for each electrocardiogram of the electrocardiogram training data to update the machine learning model using back propagation, wherein one or more weight matrices of the machine learning model are adjusted based on a confidence interval associated with the associated label for each electrocardiogram of the electrocardiogram training data.

10. The method of claim 9, further comprising:
receiving new electrocardiogram data of a subject from an electrocardiogram sensor, the new electrocardiogram data not in the electrocardiogram training data;
inputting the new electrocardiogram data into the machine learning model trained on the electrocardiogram training data to generate a new output; and
determining an indication of an analyte concentration in the subject based on the new output of the machine learning model.

11. The method of claim 10, further comprising determining a classification of the analyte concentration in the subject as high or low.

12. The method of claim 9, wherein determining a particular training label of the training labels for the plurality of electrocardiograms comprises:
  determining, for a particular electrocardiogram in the electrocardiogram training data, an estimated analyte concentration at a time the particular electrocardiogram data was generated based on the received electrocardiogram training data and the one or more analyte measurements associated with the particular electrocardiogram; and
  determining whether the particular electrocardiogram of the electrocardiogram training data satisfies a threshold to be labeled as a first classification.

13. The method of claim 9, wherein the regression line is based on a Gaussian Process Regression analysis generated based on the one or more analyte measurements associated with each of the plurality of electrocardiograms.

14. The method of claim 12, wherein determining the particular training label of the training labels for the plurality of electrocardiogram further comprises:
  determining that a confidence interval around the estimated analyte concentration of the particular electrocardiogram in the electrocardiogram training data is larger than a threshold; and
  removing the particular electrocardiogram from the plurality of electrocardiograms in response to the estimated analyte concentration being higher than a threshold.

15. The method of claim 9, wherein the analyte is one of potassium, magnesium, or calcium.

* * * * *